US006033659A

United States Patent [19]
Handelsman et al.

[11] Patent Number: 6,033,659
[45] Date of Patent: Mar. 7, 2000

[54] *BACILLUS CEREUS* STRAIN W35

[75] Inventors: Jo Handelsman; Sandra J Stewart, both of Madison, Wis.; Eric V Stabb, Honolulu, Hi.

[73] Assignee: Wisconsin Alumni Research Foundation, Madison, Wis.

[21] Appl. No.: 09/085,568

[22] Filed: May 27, 1998

[51] Int. Cl.[7] .................................................. C12N 1/20
[52] U.S. Cl. ..................................... 424/93.46; 435/252.5
[58] Field of Search ....................... 424/93.46; 435/252.5

[56] References Cited

U.S. PATENT DOCUMENTS

| | | | |
|---|---|---|---|
| 4,877,738 | 10/1989 | Handelsman et al. | 435/252.5 |
| 5,543,301 | 8/1996 | Handelsman et al. | 435/34 |
| 5,552,138 | 9/1996 | Handelsman et al. | 424/93.46 |
| 5,618,692 | 4/1997 | Handelsman et al. | 435/69.1 |
| 5,700,462 | 12/1997 | Handelsman et al. | 424/93.46 |
| 5,736,382 | 4/1998 | Handelsman et al. | 435/252.5 |

OTHER PUBLICATIONS

Raffel et al., "Genotypic and Phenotypic Analysis of Zwittermicin A–Producing Strains of *Bacillus cereus*", *Microbiology* 142:3425–3436 (1996).

Stabb et al., "Zwittermicin A–Producing Strains of *Bacillus cereus* from Diverse Soils", *Applied and Environ. Microbiology* 60(12):4404–4412 (1994).

*Primary Examiner*—Irene Marx
*Attorney, Agent, or Firm*—Ouarles & Brady LLP

[57] ABSTRACT

A novel strain of *Bacillus cereus*, designated W35 is useful as a biocontrol agent to combat fungal damping off disease in field crop plants. W35 produces the antibiotic zwittermicin A. Strain W35 is distinguished from other zwittermicin-producing *Bacillus cereus* strains by resistance to phage P7, antibiotic resistance, and colony morphology.

7 Claims, No Drawings ance 6,033,659

BACILLUS CEREUS STRAIN W35

CROSS-REFERENCE TO RELATED APPLICATIONS

Not applicable.

STATEMENT REGARDING FEDERALLY SPONSORED RESEARCH

Not applicable.

BACKGROUND OF THE INVENTION

Significant research has been conducted in recent years on the use of biological agents to increase agricultural productivity and efficiency. Biological control using microorganisms to suppress plant pests or to supplement plant growth is an attractive alternative to chemical pesticides which are less favored because of concerns about human health and environmental quality. Biological agents effective in the laboratory or in the field to combat pests or facilitate plant growth can be obtained in screening programs.

"Biological control" is defined as suppressing a pathogen using a second organism. Mechanisms of biological control are diverse. For example, certain bacteria can biologically control fungal root rot in alfalfa by competing with the fungi for space on the surface of the alfalfa roots. In contrast, a toxin produced by one species of bacteria may be used to control another species of bacteria that appears as a pathogen. Bacterially produced antibiotics are examples of such toxins. The toxin can be isolated from the species producing it and administered directly, as is the common procedure with penicillin, or the species itself may be administered under appropriate circumstances to produce the toxin in situ. Once identified, such toxins produced by soil-dwelling bacteria may have utility in diverse other areas as antifungal or antibiotic agents.

A biological control agent of scientific and economic significance is *Bacillus thuringiensis* (Bt). *B. thuringiensis* strains produce toxic proteins (Bt toxins) that specifically kill certain insects with different strains exhibited variations in target range and efficacy. In addition, methods exist for stabilizing and applying such Bt toxins, or strains harboring them, to a wide variety of field crop situations. Understanding gained by studying *B. thuringiensis* strains was largely transferable to other strains since toxins required for biological control and methods for preparing inocula for field use can be similar among strains.

A specific *Bacillus cereus* strain UW85 (ATCC 53522), has biocontrol efficacy in many applications. UW85 protects alfalfa seedlings from damping off caused by *Phytopthora medicaginis* (Pmm), protects tobacco seedlings from *Phytopthora nicotianae*, protects cucumber fruits from rot caused by *Pythium aphanidermatum*, and protects peanuts from *Sclerotinia minor*. UW85 is also described, by reference to its ATCC number in U.S. Pat. No. 4,877,738. UW85 also produces two compounds having antifungal and antibacterial activity that independently contribute to suppressing damping-off fungi. The more potent of these compounds, a novel aminopolyol is designated zwittermicin A. The second compound is kanosamine, an amino glycoside antibiotic.

BRIEF SUMMARY OF THE INVENTION

The present invention is summarized in that a *Bacillus cereus* strain having the identifying characteristics of strain W35 (ATCC No. 202074), isolated from the environment, protects and fosters the growth and establishment of alfalfa and tomato plants.

The present invention is also summarized in that a method for fostering the growth of alfalfa or tomato seedlings by applying an inoculum that includes as its active agent a novel *Bacillus cereus* isolate designated W35 (ATCC No. 202074).

Other objects, advantages, and features of the present invention will become apparent from the following specification.

BRIEF DESCRIPTION OF THE SEVERAL VIEWS OF THE DRAWINGS

Not applicable.

DETAILED DESCRIPTION OF THE INVENTION

The present invention is a substantially pure culture of a novel bacterial strain designated *Bacillus cereus* strain W35. This novel bacterial strain, which can be isolated from soil, exerts biological control over species of fungi responsible for damping off and root rot in plants. Strain W35 has been deposited in the American Type Culture Collection, 10801 University Blvd., Manassas, Va. 20110-2209, and assigned the accession number ATCC 202074.

It is anticipated that one may obtain mutants of W35 that also provide biological control comparable to that provided by W35 using standard mutagenesis and selection techniques known to one of ordinary skill in the art.

A "substantially pure" culture means a culture of a bacteria containing no other bacterial species in quantities sufficient to interfere with replication of the culture.

The *Bacillus cereus* strain W35 has biocontrol characteristics similar to those of *B. cereus* strain UW85 (ATCC 53522), described in more detail in U.S. Pat. 4,877,738 which is incorporated by reference herein in its entirety.

Strain W35 is one of a group of useful *Bacillus cereus* strains having biocontrol activity at least in part, because they naturally synthesize at least one antibiotic agent because notably an antibiotic toxin known by the coined term "zwittermicin A." This toxin is the subject of allowed patent application number 08/207,335. The antibiotic or toxin is found in supernatant fluid and other bacteria-free fluid and culture medium removed from a culture of W35 or of a protecting mutant of W35. This toxin has been so characterized as to be identifiable independent of its source in cultures of *Bacillus cereus*. Zwittermicin A is a highly water soluble molecule of about 396 daltons. The molecule includes two amino groups, and is a poly-alcohol.

Strain W35 is also characterized by resistance to phage P7, the ability to inhibit *Erwinia herbicola*, and the formation of orange colonies on MES minimal medium.

In a second aspect, the present invention is also a method of protecting plants against damping off disease where the method comprises the step of placing in the vicinity of the plant to be protected an effective quantity of a bacteria selected from the group consisting of Bacillus cereus W35 (ATCC 202074) and a mutant thereof which retains the ability to protect plants from damping off disease.

The method by which the biological control referred to in the preceding paragraph may be verified to exist is the "plant protection assay" detailed below. "Biological control" of fungi causing damping off and root rot shall be deemed to exist if, when an effective quantity of W35, or a protecting W35 mutant, an anti-fungal toxin or any other plant-protecting compound or molecule produced by W35 or a W35 mutant, or is placed in the soil or other growing medium in the immediate vicinity of the plant to be protected, a statistically significant reduction in the symptoms of damping off or root rot occurs. An "effective quantity" to combat damping off and root rot shall be that quantity sufficient to result in such a statistically significant reduction of symptoms. Clearly, if no quantity of a bacteria or any toxin or other compound is an effective quantity as so defined, that bacteria, toxin, or compound is not capable of exerting biological control over the fungi causing damping off and root rot.

Strain W35 and those of its mutants capable of exerting such biological control can be referred to collectively as "protecting" bacteria. *Bacillus cereus* antibiotic and other toxins capable of exerting such biological control can be referred to as "protecting" compounds or toxins. Plants, including seeds, seedlings, and mature plants, treated with such an effective quantity of protecting bacteria, their toxins, or *Bacillus cereus* antibiotic can be referred to as "protected" from root rot or damping off.

The following is a disclosure of the plant protection assay whereby a test material such as a bacteria, a toxin, or the like, may be tested for its ability to exert biological control over a fungus capable of causing the symptoms of damping off or root rot. The seed or seedling of the plant to be protected is planted in a planting medium in the presence of damping off or root rot causing fungi. The planting medium may be a damp soil containing such fungi, vermiculite in water with the fungi present either in the vermiculite and water or in or on the seed or seedling, an agar-based formulation, or any other planting medium in which the seed or seedling will grow and the fungi may freely develop. The bacteria, toxin, or other test material is placed at least in the immediate vicinity of the seed or seedling. Such placement shall be understood to be in the "immediate vicinity" of the seed or seedling if any soluble test material or any soluble exudate of a bacteria being tested will be in actual contact with the germinating seedling.

Preferably, if seed is used, the seed is coated with the test material, and when the test material is so used with respect to a seed, it shall be referred to hereinafter as a "seed inoculum." The process of coating seed with a seed inoculum is generally well known to those skilled in the art, and any conventional method that does not require conditions sufficiently harsh to kill bacteria or destroy toxins or other materials included in the seed inoculum is adequate. An easy and preferred method is to suspend or dissolve the test material in a 1.5% aqueous solution of methyl cellulose. For convenience, it will be presumed hereinafter that the seed inoculum is a bacteria suspended in the methyl cellulose, although a dissolvable material such as a bacterial toxin may be handled in the same manner. The plant seed to be protected is added to the suspension and is mixed vigorously with it to coat the surface of the seed with the suspension. The seed may then be dried aseptically, preferably by being placed within a laminar flow hood on a sterile surface such as a sterile petri plate. The result is a dry, seed inoculum-coated seed. When the coated seed is planted in the planting medium, the test material accompanies it to reside in the immediate vicinity of the seed.

After a time sufficient for seedling growth and the expression of the symptoms of damping off, seedlings developing from the planted seed may be evaluated for visual evidence of protection, when compared to controls. In strains of alfalfa, soybeans, and snap beans known to be vulnerable to damping off, 2 weeks of growing time in a growth chamber at 24° C. with a 12 hour photoperiod was found to be a period sufficient for the expression of symptoms of damping off when seedlings were being grown in test tubes containing roughly $10^3$ zoospores of *Pythium torulosum* or comparable, damping off-causing fungi. In strains of tomato known to be vulnerable to damping off, 9 days of growing time in a growth chamber at 24° C. with a 12 hour photoperiod was found to be a period sufficient for the expression of symptoms of damping off when seedlings were being grown in test tubes containing roughly $10^3$ zoospores of *Pythium torulosum* or comparable, damping off-causing fungi. Protected seeds developed into seedlings visually indistinguishable from uninfected seeds while control seedlings developing from unprotected seeds were killed or, in the case of snap beans, exhibited brown lesions on roots and stems, stunted roots, rotted roots, and other visually apparent symptoms of root rot.

As will become apparent below, many strains of *Bacillus cereus* are useful as biocontrol agents and produce the antibiotic zwittermicin A. See Stabb, et al., "Zwittermicin A-Producing Strains of Bacillus cereus from Diverse Soils," *Appl. Environ. Microbiol.*, 60:4404 (1954), incorporated herein by reference in its entirety. Since application of purified zwittermicin A is contemplated, it is useful to quantitatively evaluate the levels of zwittermicin A produced by the various zwittermicin A-producing strains of *B. cereus*. This permits selection of high producing strains as candidates both for fermentation production of zwittermicin A as well as mutagenesis protocols to even further increase the production of zwittermicin A.

The procedure for quantitating the level of production of zwittermicin A is generally characterized as an end point dilution, and is described in detail in Silo-Suh, *Appl. Environ. Microbiol.*, 60:2023–2030 (1994), incorporated herein S by reference in its entirety. Briefly, dilutions of partially purified zwittermicin A samples and dilutions of predetermined amounts of zwittermicin A were subjected to high voltage electrophoresis. Zwittermicin A was detected by silver staining. The amount of antibiotic in the test sample was calculated by comparison of the end-point dilution at which zwittermicin A could be detected in the test sample as compared to the standard. The general limit of detection was 0.33 $\mu$g/ml. The level of zwittermicin A production was found to vary from sample to sample, but zwittermicin production by W35 was generally comparable to the amount of zwittermicin A produced by UW85.

Using this quantitative analysis of zwittermicin A production described above, several newly isolated strains were identified which had levels of zwittermicin A production greater than UW85, ATCC 53522. In parallel testing, UW85 produced about 14 micrograms zwittermicin A per milliliter of culture. By comparison, the newly isolated strain W35 produced about 9.3 micrograms of zwittermicin A per milliliter of culture.

The *B. cereus* strain W35 (ATCC 202074) was isolated from a soil sample taken from Madison, Wis. Strain W35 is distinguishable from UW85 in that W35 is resistant to phage P7, whereas UW85 is sensitive to phage P7. In other ways, the strain resembles UW85, and it can be easily handled and grown in culture.

Zwittermicin A producing mutants of W35 include both naturally occurring and artificially induced mutants. For example, W35 is generally sensitive to the antibiotics streptomycin and tetracycline. However, it is expected that naturally occurring mutants of W35 can be isolated that exhibit resistance to one or the other of these antibiotics. Certain of these mutants may be found to produce even higher levels of zwittermicin A. Other mutants of W35 can be artificially induced by subjecting W35 to the mutagen N-methyl-nitrosoguanidine in conventional ways. Similar mutants have been made from other useful *B. cereus* strains, such as UW85 (ATCC 53522), as described in incorporated U.S. Pat. No. 4,877,738.

EXAMPLE 1

Origin of Strains

The geographic origins, and physical and chemical characteristics of the soil samples used in this study are listed in Table 1. All samples were taken from the surface horizon. Measurements of soil pH, organic matter, and the particle size were made by the University of Wisconsin Soil & Plant Analysis Laboratory (Madison, Wis.).

TABLE 1

Characteristics of soils used in this study

| Soil/Site | Country | pH | % Organic[a] | % Sand, Silt, Clay[b] | Most recent vege-tation |
|---|---|---|---|---|---|
| Lutz | Panama | nd[c] | 5.5 | nd | Forest |
| Snyder-Molino | Panama | nd | 6.2 | nd | Forest |
| Barbour-Lathrop | Panama | nd | 7.1 | nd | Forest |
| Moroceli | Honduras | nd | 1.7 | nd | Maize-Beans |
| San Matias | Honduras | 5.8 | 1.5 | nd | Maize-Beans |
| LaVega1 | Honduras | 6.3 | 2.3 | nd | Beans |
| LaVega5 | Honduras | 5.9 | 2.5 | nd | Sorghum-Maize |
| Arlington WI | USA | 6.9 | 4.2 | 23, 68, 9 | Alfalfa |
| Hancock WI | USA | 6.6 | 0.8 | 87, 8, 5 | Alfalfa-Oats |
| Marshfield WI | USA | 6.5 | 3.1 | 23, 72, 5 | Alfalfa |
| Lancaster WI | USA | 7.1 | 2.3 | 19, 68, 13 | Alfalfa |
| Madison WI | USA | 7.0 | 3.2 | 27, 56, 17 | Alfalfa |
| Taos NM | USA | 8.1 | 4.3 | nd | Pasture |
| Tifton GA | USA | 6.3 | 1.0 | 87, 12, 1 | Tobacco |
| Douglas Gully | Australia | 6.1 | 2.2 | nd | Vineyard |
| Lelystad | Netherlands | 7.5 | 1.8 | 51, 36, 13 | Potatoes |

[a]Organic matter content determined by measuring loss of weight after ignition.
[b]Sand, silt and clay contents were determined by hydrometer measurements.
ND, not determined.

TABLE 2

Strains and isolates used in this study

| Strain(s)/Isolates | Origin |
|---|---|
| ATCC7064, ATCC27877, ATCC12826 | American Type Culture Collection |
| BGSC6A3, BGSC6E1, BGSC6E2, BGSC4A9, BGSC4B1, BGSC4C3, HD1, BGSC4E1, BGSC4F1, BGSC4G1, BGSC4H1, BGSC4I1, BGSC4J1, BGSC4S2 | Bacillus Genetic Stock Center |
| T | U.W. Bacteriology Dept. Collection |
| UW85 | Alfalfa root. Arlington. WI (26) |
| Soy130 | Soybean root, Walnut St. Farm, Madison. WI |
| ALF1, ALF9, ALF10, ALF13, ALF19, ALF23, ALF52, ALF53, ALF79, ALF83, ALF85, ALF94, ALF95, ALF98, ALF99, ALF108, ALF109, ALF115, ALF117, ALF133, ALF137, ALF144, ALF154, ALF157, ALF161, ALF166, ALF167, | Roots of alfalfa plants planted in soil from Arlington, WI and grown in growth chamber |

TABLE 2-continued

Strains and isolates used in this study

| Strain(s)/Isolates | Origin |
| --- | --- |
| ALF173 | |
| LUTZ21, LUTZ58, LUTZ128 | Lutz soil |
| SNY14, SNY42, SNY44, SNY45, SNY73 | Snyder-Molino soil |
| BAR78, BAR145, BAR177 | Barbour-Lathrop soil |
| MOR1, MOR28, MOR37 | Moroceli soil |
| SM32, SM43, SM44 | San Matias soil |
| VGA19, VGA118, VGA137 | Lavegal soil |
| VGA562, VGA577, VGA598 | LaVega5 soil |
| AS7-4, AS8-4, AG8-13, AS4-12, ARL8 | Arlington soil |
| HS1-3, HS23-11, HS24-8, HS24-9 | Hancock soil |
| MS1-9, MS3-2, MS8-2 | Mansfield soil |
| LS2-2, LS2-12, LS33-2 | Lancaster soil |
| WS4-12, WS8-8, WS10-15, WS16-4, WS22-12 | Madison soil |
| TNM68, TNM155, TNM243 | Taos soil |
| TG38, TG42, TG126 | Tifton soil |
| DGA34, DGA37, DGA84, DGA94 | Douglas Gully soil |
| LN24, LN75, LN100 | Lelystad soil |
| Z8 | Zamorano, Honduras soil |
| W35 | West Madison farm site, Madison WI |

Based on the profiles of fatty acids from 47 isolates analyzed by Five Star Labs (Branford Conn.) and Microbial ID (Newark Del.), all of the isolates were classified as members of the *B. cereus* group, which includes the species *B. mycoides*, *B. anthracis* and *B. thuringiensis*. The unique rhizoidal morphology of *B. mycoides* strains differentiates them from *B. cereus*, and none of the isolates in this collection display *B. mycoides*-like morphology. *B. anthracis* is not hemolytic and is usually sensitive to ampicillin and therefore was probably excluded from this collection. Differentiation between *B. cereus* and *B. thuringiensis* is difficult with standard methods. Therefore we have followed current recommendations and considered all isolates gathered in this study as *B. cereus*. Strains BGSC4A9, BGSC4B1, BGSC4C3, HD1, BGSC4E1, BGSC4F1, BGSC4G1, BGSC4H1, BTSC4Il, BGSC4J1 and BGSC4S2 were previously classified by others as *B. thuringiensis*, and that species designation was retained for those strains.

Assay for sensitivity to phage P7

The phages P7 (ATCC 75237) and PB were used to help characterize the strains. The susceptibility of *B. cereus* strains to infection by phage P7 has proven to have a strong correlation to biocontrol utility and antibiotic production. To propagate these phages, we spread a mixture of melted soft agar (4 g agar/l) with approximately $10^6$ PFU of phage and an excess of *B. cereus* strain UW85 on ½-strength TSA plates. Plates were incubated overnight at 28° C. and then the soft agar was scraped off the plates and suspended in ½-strength trypticase soy broth (½-strength TSB), (1 ml/plate). Agar and cells were removed by centrifugation, and the supernatant solution was passed through a 0.2 $\mu$m filter. Phage titers were typically $1\times10^{10}$ PFU/ml.

To screen large numbers of isolates for P7 sensitivity, grids of 48 isolates were grown on 1/10-strength TSA and then cells were transferred with a metal replicator onto 1/10-strength TSA plates that had been spread with dilutions of P7 such that they contained approximately $10^8$, $10^4$, and $10^3$ PFU/plate. A 1/10-strength TSA plate containing no phage was used as a control. Isolates that appeared to form patches with decreased growth or plaques on plates containing P7 were tested in the soft-agar overlay assay (described below) to determine if they were $P7^s$. Most isolates that were $P7^r$ in the primary screen were not re-tested.

In the second test for sensitivity of bacterial isolates to P7, each isolate was grown on ½-strength TSA and cells were scraped off plates and mixed in soft agar overlays to form lawns on fresh ½-strength TSA plates. Ten-fold dilutions of P7 were placed in 5-$\mu$l drops on the plates, which were then incubated at 28° C. If plaques appeared, the strain was designated P7-sensitive ($P7^s$). Lawns of two isolates, ARL8 and HS23-11, were cleared by undiluted drops of P7, but P7 did not form isolated plaques on these isolates at lower concentrations. The clearing due to high titer drops appeared to be due to P7 rather than a chemical present in UW85 lysates, since high titer drops of lysates of PB, which produces turbid plaques on UW85, did not cause clearing on lawns of ARL8 and HS23-11. Therefore these strains were also scored $P7^s$. Isolates whose lawns appeared unaffected by P7 were scored $p_7^r$.

Assay for inhibition of *Erwinia herbicola*

Inhibition of *E. herbicola* LS005 was assayed as described in Silo-Suh et al. *Appl. Environ. Microbiol.,* 60:2023–2030 (1994), with the following modifications. Three-day-old cultures of each *B. cereus* isolate grown in ½-strength TSB were tested to determine whether they inhibited *E. herbicola* on 1/1000-strength TSA plates. Isolates that produced visible zones of inhibition of *E. herbicola* were tested again. Isolates that produced visible zones of inhibition in both tests were scored $Eh^+$. Isolates that did not noticeably inhibit *E. herbicola* in each of two initial tests were scored $Eh^-$. Some *B. cereus* isolates did not inhibit *E. herbicola* during initial testing but did after storage at −20° C., and certain isolates (ALF115,HD1 and BGSC4S2) had variable phenotypes producing either small zones of inhibition or no zone in subsequent tests; these were classified $Eh^-$.

Assay for zwittermicin A and kanosamine

Zwittermicin A and kanosamine were identified in culture supernatants by cation exchange chromatography using CM SEP-PAK cartridges (Millipore, Millford, Mass.) followed by high voltage paper electrophoresis (HVPE). The cation fraction from the equivalent of 4 ml of culture supernatant was applied to the paper, which was stained with silver nitrate after electrophoresis, described in Silo-Suh et al. supra. Isolates that produced material indistinguishable from either authentic zwittermicin A or authentic kanosamine in HVPE were designated zwittermicin A producers or kanosamine producers, respectively. To verify the structural identity of zwittermicin A produced by nine representatives of the collection of isolates, putative zwittermicin A was purified from these isolates, and subjected to proton nuclear magnetic resonance spectroscopy ($^1$H-NMR) and fast atom bombardment mass spectrometry.

Assay for suppression of alfalfa or tomato damping-off

Bacterial isolates were grown for four days in ½-strength TSB with vigorous shaking at 28° C. and tested in an assay for damping-off. Seeds of alfalfa variety Webfoot MPR or tomato variety Wisconsin 55 were placed in a cell of a 96-cell bedding plant container containing sterilized vermiculite and inoculated with an aliquot of a Bacillus culture and zoospores from either *Pythium torulosum* or spores of *Fusarium oxysporum* f. sp. *radicis-lycopersici* (FORL). Statistical analyses (analysis of variance, Dunnet's comparison test, standard error of least squared mean) were conducted using the SAS Computer Program. The results of these experiments are summarized in Tables 3–9.

The results obtained from the plant protection assays indicate that for protection of tomato plants against damping off and root rot, inoculating the soil in which the seeds are planted with *B. cereus* culture is more effective than coating the seed with the bacterial inoculum. Tomato seedlings grown from seeds coated with a plant protective strain of *B. cereus* did not exhibit increased resistance to disease relative to seedlings grown from untreated seeds.

TABLE 3

Disease suppression by Bacillus strains

| Treatment* | Alfalfa seedling survival (%)** Experiment 1 | Experiment 2 | Experiment 3 |
|---|---|---|---|
| untreated (−zoospores) | 59.2 ± 4.3 A | 41.7 ± 5.0 AB | 65.0 ± 4.1 A |
| untreated (+zoospores) | 2.5 ± 0.67 E | 18.1 ± 3.8 D | 3.5 ± 1.2 E |
| *B. cereus* UW85 | 13.1 ± 1.9 BC | 46.2 ± 3.3 A | 32.4 ± 3.5 C |
| *B. cereus* UW030 | 6.9 ± 1.1 D | 27.5 ± 4.9 C | 5.0 ± 1.2 E |
| *B. cereus* MOR28 | 15.6 ± 2.4 BC | 47.1 ± 4.4 A | 21.3 ± 3.8 D |
| *B. cereus* SOY130 | 20.0 ± 2.7 B | 32.3 ± 3.9 BC | 23.3 ± 3.8 D |
| *B. lichenitormis* DA33 | 3.7 ± 1.1 E | NT | NT |
| *B. laevolacticus* SB3006 | 13.1 ± 2.1 C | NT | 22.4 ± 4.4 D |
| *B. cereus* W35 | NT | 45.2 ± 4.7 A | 23.5 ± 4.3 D |
| *B. cereus* Z8 | NT | 49.4 ± 4.2 A | 44.4 ± 4.3 B |
| p(trt) | .0001 | .0001 | .0001 |
| p(blk) | .2936 | .0049 | .0001 |
| p(rep) | .9869 | .8432 | .3997 |

*1 ml of culture grown in 1/2X TSB for four days with vigorous shaking at 28°.
**plants were inoculated with 250 or 500 *Pythium torulosuin* zoospores in Experiment 1; 300 zoospores in Experiment 2; 250, 500, or 750 zoospores in Experiment 3, and scored 10 days after inoculation.
10 seeds of alfalfa variety Webfoot MPR were placed in a cell of a 96-cell bedding plant container containing sterilized vermiculite and inoculated with the Bacillus and *Pythium*.
In Experiments 1 and 2, each treatment consisted of four blocks each containing four replicates with three cells in each replicate; therefore each value represents survival among seedlings from 480 seeds. In experiment 3, each treatment consisted of six blocks each containing three replicates with three cells in each replicate; therefore each value represents survival among seedlings from 540 seeds.
For each Experiment, the values were calculated over all levels of zoospore concentration since there were no significant differences in survival due to zoospore concentration.

TABLE 4

Suppression of disease caused by *Pythium torulosum* by Bacillus strains

| Bacterial Treatment[a]* | Tomato seedling emergence (%)[b] 10 zoospores/seed | 20 zoospores/seed | Average[c] |
|---|---|---|---|
| none | 28.8 ± 8.0 B | 23.3 ± 6.6 C | 26.1 ± 5.0 C |
| UW85 | 90.8 ± 2.1 A | 90.4 ± 1.8 A | 90.6 ± 1.4 AB |
| UW030 | 93.7 ± 1.3 A | 77.1 ± 5.9 B | 85.4 ± 3.2 B |
| MOR28 | 91.7 ± 1.7 A | 92.9 ± 1.6 A | 92.3 ± 1.1 A |
| SOY130 | 91.7 ± 1.8 A | 88.7 ± 2.3 A | 90.2 ± 1.4 AB |
| W35 | 92.9 ± 1.7 A | 91.2 ± 1.5 A | 92.1 ± 1.1 A |
| Z8 | 89.6 ± 1.5 A | 93.3 ± 1.3 A | 91.4 ± 1.0 AB |
| 5B3006 | 94.2 ± 1.7 A | 94;2 ± 1.8 A | 94.2 ± 1.2 A |

[a]1.0 ml of Bacillus culture grown in 1/2X TSB for four days with vigorous shaking at 28° C. was added to each cell.
[b]10 seeds of tomato variety Wisconsin 55 were placed in a cell of a 96-cell bedding plant container containing sterilized vermiculite and inoculated with the Bacillus culture. The bottom of the flat was flooded with water containing enough zoospores for 10 or 20 zoospores per seed. Each treatment at each zoospore level consisted of two blocks each containing 12 replicates; therefore each value represents the % emergence among seedlings from 240 seeds 30 days after inoculation.
[c]Average % emergence of tomato seedlings of both zoospore levels; values followed by the same letter do not differ significantly at P = 0.05.

TABLE 5

Suppression of disease caused by *Pythium torulosum* by Bacillus strains

| Bacterial Treatment[a] | Tomato seedling health (%)[b] 10 zoospores/seed | 20 zoospores/seed | Average[c] |
|---|---|---|---|
| none | 26.9 ± 7.8 B | 16.7 ± 5.9 C | 21.7 ± 4.8 C |
| UW85 | 88.3 ± 2.2 A | 87.1 ± 2.4 A | 87.7 ± 1.6 A |
| UW030 | 90.8 ± 2.0 A | 70.0 ± 6.6 B | 80.4 ± 3.7 B |
| MOR28 | 87.9 ± 2.1 A | 92.1 ± 1.5 A | 90.0 ± 1.3 A |
| SOY130 | 90.4 ± 1.8 A | 85.8 ± 2.6 A | 88.1 ± 1.6 A |
| W35 | 90.4 ± 2.1 A | 87.9 ± 1.9 A | 89.2 ± 1.4 A |
| Z8 | 87.5 ± 1.8 A | 86.2 ± 2.4 A | 86.9 ± 1.4 AB |
| SB3006 | 90.4 ± 2.3 A | 90.8 ± 1.9 A | 90.6 ± 1.5 A |

[a]1.0 ml (~$10^9$ cfu) of Bacillus culture grown in 1/2X TSB for four days with vigorous shaking at 28° C. was added to each cell.
[b]10 seeds of tomato variety Wisconsin 55 were placed in a cell of a 96-cell bedding plant container containing sterilized vermiculite and inoculated with the Bacillus culture. The bottom of the flat was flooded with water containing enough zoospores for 10 or 20 zoospores per seed. Each treatment at each zoospore level consisted of two blocks each containing 12 replicates; therefore each value represents the % healthy seedlings from 240 seeds 30 days after inoculation.
[c]Average % healthy tomato seedlings of both zoospore levels; values followed by the same letter do not differ significantly at P = 0.05.

TABLE 6

Suppression of disease caused by *Fusarium oxysporum* f. sp. *radicis-lycopersici* (FORL) by bacterial strains.

| Treatment[a] | % Emergence[b] | % Healthy[c] |
|---|---|---|
| Untreated | 90.6 ± 2.9 A | 87.5 ± 2.9 A |
| AS4-12 D | 63.1 ± 4.1 B | 52.2 ± 4.3 B |
| No. 11 D | 29.7 ± 4.7 C | 20.6 ± 4.1 C |
| SOY130 | 28.7 ± 4.3 CD | 18.7 ± 3.9 C |
| W35 | 27.5 ± 4.1 CD | 18.1 ± 3.4 C |
| MS1-9 | 24.3 ± 4.1 CDE | 16.9 ± 3.8 C |
| UW030 | 23.4 ± 3.9 CDE | 13.7 ± 3.0 C |
| UW85 | 21.5 ± 4.7 CDE | 13.1 ± 3.8 C |
| Z8 | 20.6 ± 3.6 CDE | 14.7 ± 3.0 C |

TABLE 6-continued Suppression of disease caused by *Fusarium oxysporum* f. sp. *radicis-lycopersici* (FORL) by bacterial strains.

| Treatment[a] | % Emergence[b] | % Healthy[c] |
|---|---|---|
| MOR28 | 19.4 ± 3.2 DE | 12.5 ± 2.7 C |
| AS4-12 | 19.1 ± 3.9 DE | 13.7 ± 3.0 C |
| water | 17.2 ± 3.2 E | 11.5 ± 2.9 C |

[a]Tomato seeds coated with $10^5$ Bacillus spores or a drench (D) of 1.0 ml (~$10^9$ cfu) from a four-day-old culture. Strain No. 11 is *Bacillus polymyxa*, all other strains are *Bacillus cereus*.
[b]10 seeds of tomato variety Wisconsin 55 were planted in a cell of a 96-cell bedding plant container containing sterilized vermiculite and the drench treatments applied. 5000 Fusarium spores were inoculated into each cell. Each treatment consisted of 4 blocks each containing 8 replicates; therefore each value represents the mean ± se % emergence from 320 seeds 24 days after inoculation. Means with the same letter are not significantly different at $P = 0.05$.
[c]The mean ± se % healthy plants 24 days after inoculation; values followed with the same letter do not differ significantly at $P = 0.05$.

TABLE 7

Suppression of disease caused by *Fusarium oxysporum* f. sp. *radicis-lycopersici* (FORL) by bacterial strains

| Treatment[a] | Inhibition of *Erwinia herbicola*[b](mm) | Inhibition of FORL[c](mm) | % Emergence[d] | % Healthy[e] |
|---|---|---|---|---|
| Z8 | 7.5 | 3* | 88.6 ± 2.7 A | 83.3 ± 3.3 A |
| UW85 | 9 | 3* | 87.6 ± 2.7 AB | 81.4 ± 2.5 AB |
| No. 6 | 0 | 3.5 | 86.2 ± 2.7 AB | 79.0 ± 2.9 ABC |
| UW030 | 0 | 0 | 81.4 ± 3.3 AB | 76.2 ± 3.8 ABC |
| W35 | 6 | 2.5* | 80.5 ± 3.3 AB | 73.3 ± 3.8 ABC |
| MOR28 | 10 | 3* | 79.5 ± 4.0 AB | 70.9 ± 4.2 ABCD |
| AS4-12 | 9 | 4* | 77.1 ± 4.5 ABC | 68.6 ± 4.7 CD |
| SOY130 | 8.5 | 5* | 75.7 ± 5.6 BC | 69.0 ± 6.5 BCD |
| W1 | 0 | 6.5 | 66.2 ± 6.5 CD | 60.0 ± 6.9 DE |
| MS1-9 | 10.5 | 4* | 65.7 ± 4.9 CD | 55.2 ± 4.9 EF |
| No. 9 | 0 | 0 | 61.9 ± 5.4 D | 52.4 ± 4.9 EFG |
| No. 11 | 0 | 0 | 56.2 ± 5.1 DE | 45.2 ± 4.5 FG |
| water | 0 | 0 | 47.6 ± 6.0 E | 41.4 ± 5.8 G |

[a]1.0 ml of culture grown in 1/2X TSB for four days with vigorous shaking at 28° C. was added to each cell. All strains are *Bacillus cereus* except No. 6 and No. 9 are Xanthomonas, No. 11 is *Bacillus polymyxa*, and W1 is Pseudomonas.
[b]$10^5$ *Erwinia herbicola* cells are spread on a .001X TSA plate. A 8 mm well was cut into the agar and filled with 100 µl of culture. Zones of inhibition were measured after 3 days. Values represent the mean of two zones.
[c]$10^4$ FORL spores were spread onto a Potato Dextrose Agar plate. A 8 mm well was cut into the agar and filled with 100 µl of culture. Zones of inhibition were measured after 3 days. *Not a clear zone, growth of FORL was slowed within the zone. Values represent the means of two zones.
[d]10 seeds of tomato variety Wisconsin 55 were planted in a cell of a 96-cell bedding plant container containing sterilized vermiculite and inoculated with the bacterial culture. 5000 Fusariwn spores were inoculated into each cell. Each treatment consisted of 3 blocks each containing 7 replicates; therefore each value represents the mean ± se % emergence from 210 seeds 29 days after inoculation. A control of 70 untreated seeds showed a 95.7% emergence. Means with the same letter are not significantly different at $P = 0.05$.
[e]The mean ± se % healthy plants 29 days after inoculation.

TABLE 8

Disease suppression of *Pythium torulosum* by Bacillus strains

| Treatment[a] | Erwinia zone of inhibition (mm)[b] | Tomato seedling survival (%)[c] | | |
|---|---|---|---|---|
| | | 10 zoospores/seed | 20 zoospores/seed | Average[d] |
| untreated | | 26.2 ± 6.6 | 18.3 ± 5.0 | 22.3 ± 4.1 |
| UW85 | 11 | 87.9 ± 2.9 | 81.2 ± 4.8 | 84.6 ± 2.8 |
| UW030 | 0 | 88.3 ± 2.7 | 74.5 ± 6.2 | 81.9 ± 3.4 |
| MOR28 | 12 | 90.0 ± 2.2 | 90.8 ± 2.8 | 90.4 ± 1.7 |
| SOY130 | 10 | 89.6 ± 1.7 | 82.5 ± 4.8 | 86.0 ± 2.5 |
| W35 | 8 | 93.3 ± 1.6 | 87.1 ± 3.9 | 90.2 ± 2.1 |
| Z8 | 8 | 87.5 ± 2.1 | 91.2 ± 2.1 | 89.4 ± 1.4 |
| SB3006 | 11 | 91.2 ± 2.5 | 92.1 ± 1.8 | 91.7 ± 1.5 |

[a]1.0 ml of culture grown in 1/2X TSB for four days with vigorous shaking at 28° C.
[b]$10^5$ Erwinia cells were spread onto a water agar plate. 0.1 ml of Bacillus culture was placed in an 8 mm well cut in the agar. Zones of inhibition were scored after 6 days.
[c]10 seeds of tomato variety Wisconsin 55 were placed in a cell of a 96-cell bedding plant container containing sterilized vermiculite and inoculated with the Bacillus culture. The bottom of the flat was flooded with water containing enough zoospores for 10 or 20 zoospores per seed. Each treatment at each zoospore level consisted of two blocks each containing 12 replicates; therefore each value represents the survival among seedlings from 240 seeds 9 days after inoculation.
[d]Average survival of tomato seedlings over both zoospore levels.

TABLE 9

Disease suppression of *Pythium torulosum* by Bacillus strains

| Treatment | Tomato seedling survival (%)[a] | | |
|---|---|---|---|
| | 0 zoospores/seed | 25 zoospores/seed | 75 zoospores/seed |
| untreated | 87.2 ± 2.3 | 5.0 ± 1.2 | 0 ± 0 |
| UW85 | 93.8 ± 1.5 | 2.2 ± 1.8 | 0 ± 0 |
| UW030 | 91.1 ± 2.3 | 0 ± 0 | 0 ± 0 |
| MOR28 | 87.2 ± 2.8 | 7.8 ± 5.8 | 0 ± 0 |
| SOY130 | 91.1 ± 2.5 | 0 ± 0 | 0 ± 0 |
| W35 | 92.8 ± 2.7 | 3.9 ± 2.9 | 0 ± 0 |
| Z8 | 87.2 ± 2.6 | 4.4 ± 4.6 | 0 ± 0 |
| SB3006 | 89.4 ± 2.3 | 5.5 ± 5.1 | .55 ± .57 |

[a]10 seeds of tomato variety Wisconsin 55 coated with a Bacillus strain were placed in a cell of a 72-cell bedding plant container containing sterile vermiculite. The flat was flooded with water containing zoospores. Each treatment consisted of two blocks each containing 9 replicates; therefore each value represents the survival among seedlings from 180 seeds after 12 days of growth.

Testing diversity of strains

To estimate the diversity of zwittermicin A and kanosamine-producers, we sought to determine the minimum number of unique zwittermicin A and/or kanosamine-producing strains in our collection. We considered isolates to be distinct strains only if phenotypic differences between them could be shown. Therefore, isolates were subjected to a series of phenotypic tests. All characterization was performed on isolates that had been colony purified on ½-strength TSA. To test for antibiotic resistance, isolates were streaked on ½-strength TSA containing tetracycline (10 μg/ml), neomycin (5 μg/ml), or streptomycin (10 μg/ml), and incubated at 28° C. overnight. Isolates that grew similarly when streaked in the presence or absence of antibiotic were classified as antibiotic resistant. To test isolates for pigment production, they were grown on MES minimal medium at 28° C. for seven days and then scored visually. MES minimal medium contained 9.75 g/L 2-[N-morpholine]ethan-sulfonic acid (MES), 2 g/L $(NH_4)_2SO_4$, 0.2 g/L $MgSO_4.7 H_2O$, 0.25 mg/L $MnSO_4.7 H_2O$, 1.25 g/L $K_2HPO_4.3H_2O$, 2 g/L L-glutamic acid, 10 mg/L thiamine, 15 g/L agar, 40 mg/L $FeCl_3.6H_2O$, 5 g/L sucrose and 1 mM of the amino acids threonine, serine, leucine, valine, and alanine, and was adjusted to pH 6.1. MES-Thr medium was MES minimal medium lacking threonine. We characterized the ability of isolates to grow on MES-Thr media by streaking isolates onto MES-Thr plates and incubating at 28° C. for four days and recording the rate of appearance of colonies for each strain. Phages ΦATCC 7064 and ΦATCC 27877 were obtained from the American Type Culture Collection and were propagated on bacterial strains ATCC 7064 and ATCC 27877, respectively. Phage Φ63 was propagated on strain Bt-1, and both Φ63 and Bt-1 were obtained from R. Landen. Sensitivity of isolates to phages Φ63, ΦATCC7064 and ΦATCC27877 was determined by the soft-agar overlay method described above for P7, with plaque formation as the indicator of sensitivity. The results of these studies are summarized in Tables 10 and 11.

Association of zwittermicin A production with P7$^s$ and Eh$^+$ isolates

It was known that *B. cereus* strain UW85 produces two antibiotics, the novel aminopolyol, zwittermicin A, and kanosamine, that contribute to the suppression of alfalfa seedling damping-off. UW85 was originally identified in a labor-intensive screen for biological control activity. The study conducted above was intended to investigate whether sensitivity to P7 (P7$^s$) and the ability to inhibit *E. herbicola* (Eh$^+$) were phenotypes that could be used to identify zwittermicin A producers and useful biocontrol strains.

4,307 *B. cereus* and *B. thuringiensis* isolates were screened for P7$^s$ and/or Eh$^+$ phenotypes. The isolates were obtained from geographically diverse soil samples collected at a total of 16 locations in five countries (Table 1 above), from alfalfa and soybean roots, and from stock culture collections (Table 2 above). the number of P7$^s$ or P7$^r$Eh$^+$ isolates identified from each source and the number of isolates tested were tabulated. P7$^s$ isolates were identified in samples from 14 of the 16 soils examined as well as from alfalfa and soybean roots. Of the 87 P7$^s$ isolates, all were Eh$^+$ except SNY73 and LN100. P7$^s$Eh$^+$ isolates were identified from each of the soils as well as from alfalfa roots. Among all the isolates tested, approximately 2% (85/4,307) of the isolates examined were P7$^s$Eh$^+$ and 7% (132/1,876) were P7$^r$Eh$^+$.

Quantitative comparison of zwittermicin A production

This quantitative comparison was performed by the end-point dilution analysis described above. The results indicate that W35 produces zwittermicin A at levels comparable to UW85.

TABLE 10

Characteristics that differentiate *Bacillus cereus* strains

| Strains | ZmA[a] concentration μg/ml | P7[b] | Str[c] | Neo[c] | Tet[c] | Colony Color on MES | Colony Morphology | Erwinia herbicola inhibition zone[d] (mm) |
|---|---|---|---|---|---|---|---|---|
| UW65 | 14.6 ± 1.1 | S | S | S | S | orange | opaque | 11.7 ± 1.7 |
| MOR2B | ND | S | S | S | S | orange | opaque | 10 ± 0 |
| AS4-12 | ND | S | S | S | S | orange | opaque | ND |
| DGA34 | ND | S | S | S | S | orange | clear | ND |
| SOY130 | ND | S | R | R | S | orange | opaque | ND |
| Z8 | 17.4 ± 3.7 | R | S | ND | S | white | opaque | 7 ± 0.8 |
| W35 | 9.3 ± 1.0 | R | S | ND | S | orange | opaque | 9 ± 2.2 |
| MS1-9 | ND | S | S | S | S | orange | opaque | ND |
| UW030 | 0 | S | R | S | R | orange | opaque | ND |

[a]Concentration of zwittermicin in culture filtrate determined by end-point dilution method of Silo-Suh et al. (1994)
ND = not determined.
[b]S and R indicate sensitivity and resistance to phage P7.
[c]Streptomycin at 10 μg/ml, neomycin at 5 μg/ml, and tetracycline at 10 μg/ml. S and R indicate sensitivity and resistance to streptomycin, neomycin, and tetracycline.
[d]Inhibition zone size measured from edge of well containing *B. cereus* strain.

TABLE 11

Erwinia inhibition on 1/1000X TSA

| | Zone size (mm)** | | |
|---|---|---|---|
| Strain* | Experiment 1 | Experiment 2 | Experiment 3 |
| none | 0 | 0 | 0 |
| DA33 | 0 | NT | NT |
| UW8S | 4 | 5.5 | 8 |
| SOY130 | 5.3 | 5 | 8 |
| MOR28 | 6 | 5 | 9 |
| UW030 | 0 | 0 | 0 |
| SB3006 | 5 | NT | 8 |
| W35 | NT | 3 | 3 |
| Z8 | NT | 5 | 6 |

*All Bacillus cultures were grown in 1/2X TSB for four days with vigorous shaking at 280. Erwinia was grown in 1/2X TSB overnight.
$10^5$ Erwinia cells were spread on each plate.
50 μl of the Bacillus culture to be tested was placed in a 6-mm well; except in Experiment 3, 100 μl was placed in well.
All Bacillus cultures were fully sporulated except DA33, which did not produce spores under these conditions.
Zones of inhibition were scored after 1 day.
**Each value represents the mean of three zones for experiment 1, two zones for experiment 2, and one zone for experiment 3.

What is claimed is:

1. A biologically pure culture of a *Bacillus cereus* strain having all of the identifying characteristics of *Bacillus cereus* strain W35 ATCC 202074.

2. The culture of claim 1, wherein the strain is W35 ATCC 202074.

3. A biologically pure culture of a mutant of *Bacillus cereus* strain W35 ATCC 202074 the mutant strain retaining the ability to produce protects a plant against damping off disease.

4. The culture of claim 3, wherein the plant is an alfalfa plant.

5. The culture of claim 3, wherein the plant is a tomato plant.

6. An inoculum for application to a plant comprising a carrier and bacteria in a quantity effective to protect the plant from damping off disease, the bacteria selected from the group consisting of a *Bacillus cereus* having all of the identifying characteristics of *Bacillus cereus* W35 ATCC 202074 and a mutant of *Bacillus cereus* W35 ATCC 202074 which produces zwittermicin A and protects the plant against damping off disease.

7. A method for protecting plants growing in a medium from damping off disease comprising the steps of placing at least in the immediate vicinity of the plant to be protected an effective quantity of a bacteria selected from the group consisting of *Bacillus cereus* W35 (ATCC 202074) and a mutant thereof retaining the ability to produce zwittermicin A and the ability to protect plants from damping off disease.

* * * * *

UNITED STATES PATENT AND TRADEMARK OFFICE
CERTIFICATE OF CORRECTION

PATENT NO. : 6,033,659
DATED : March 7, 2000
INVENTOR(S) : Jo Handelsman, et al

It is certified that error appears in the above-identified patent and that said Letters Patent is hereby corrected as shown below:

In the specification, page 1, line 10, delete "Not applicable." and insert therefor:

--This invention was made with United States government support awarded by the following agencies:

AID Grant No: DHR-5600-G-00-0100-00
EPA Grant No: CR 822902-01-0
NSF Grant No: DUE-9156087
USDA AGRICCREE #:93-37305-9236;92-34103-7170;
94-39210-0559; 94-37313-0676; HATCH D676
USDA2 USDA GRANT# IR4 94-34108-0002; (SUNJ GRANT# CK479673)
USDA3 USDA# 94-34190-1204; 92-34190-6941;(Purdu# 593-0213-15; 593-0130-16)

The United States Government has certain rights in this invention.--

Signed and Sealed this

Eighth Day of May, 2001

Attest:

NICHOLAS P. GODICI

Attesting Officer
Acting Director of the United States Patent and Trademark Office